(12) United States Patent
Humble et al.

(10) Patent No.: US 6,734,141 B2
(45) Date of Patent: May 11, 2004

(54) USE OF NON-SPREADING SILICONE SURFACTANTS IN AGROCHEMICAL COMPOSITIONS

(75) Inventors: Geoffrey David Humble, Chesterfield, VA (US); Michael Wayne Kennedy, Glen Allen, VA (US); Jörg Simpelkamp, Richmond, VA (US)

(73) Assignee: Goldschmidt AG, Essen (DE)

( * ) Notice: Subject to any disclaimer, the term of this patent is extended or adjusted under 35 U.S.C. 154(b) by 21 days.

(21) Appl. No.: 09/991,593

(22) Filed: Nov. 23, 2001

(65) Prior Publication Data

US 2003/0104944 A1 Jun. 5, 2003

(51) Int. Cl.$^7$ ............................................... A01N 25/30
(52) U.S. Cl. ...................................... 504/206; 504/355
(58) Field of Search ................................. 504/206, 358

(56) References Cited

U.S. PATENT DOCUMENTS

| | | | |
|---|---|---|---|
| 5,017,216 A | 5/1991 | Petroff et al. ................. | 71/116 |
| 5,059,704 A | * 10/1991 | Petroff et al. ................ | 556/437 |
| 5,104,647 A | 4/1992 | Policello ...................... | 514/772 |
| 5,145,977 A | 9/1992 | Petroff et al. ................ | 556/437 |
| 5,145,978 A | 9/1992 | Petroff et al. ................ | 556/437 |
| 5,204,438 A | 4/1993 | Snow et al. ................... | 528/25 |
| 5,558,806 A | 9/1996 | Policello et al. ............. | 252/355 |
| 5,821,195 A | 10/1998 | Sandbrink et al. ........... | 504/206 |
| 5,985,793 A | 11/1999 | Sandbrink et al. ........... | 504/116 |
| 6,040,272 A | 3/2000 | Riego et al. ................. | 504/206 |
| 6,051,533 A | 4/2000 | Kajikawa et al. ............ | 504/206 |

FOREIGN PATENT DOCUMENTS

| | | |
|---|---|---|
| EP | 0 355 650 | 2/1990 |
| EP | 0 483 095 | 4/1992 |
| GB | 1 255 249 | 12/1971 |
| JP | 05 025010 | 2/1993 |
| WO | WO 89/12394 | 12/1989 |
| WO | WO 99/40785 | 8/1999 |

OTHER PUBLICATIONS

"Adjuvants for Herbicides", Weed Science Society of America Monograph Series, No. 1, 1982, R.H. Hodgsen; p. i–ii.
Noll, Walter; "Chemistry and Technology of Silicones", 2$^{nd}$ Edition, 1968, Academic Press, pp. 373–381.

Field and Bishop, "Promotion of Stomatal Infiltration of Glyphosate by an Organosilicone Surfacant Reduces the Critical Rainfall Period", Pestic. Sci. 1988, 24, pp. 55–62.
Stevens et al, "Contributions of Stomatal Infiltration and Cuticular Penetration to Enhancements of Foliar Uptake by Surfacants", Pestic. Sci., 1991, 33, 371–382.
Gaskin and Stevens, "Antagonism of the Foliar Uptake of Glyphosate into Grasses by Organosilicone Surfacants. Part 1: Effects of Plant Species, Formulation, Concentrations and Timing of Application", Pestic. Sci. 1993, 38, pp. 185–192.
Gaskin and Stevens, "Antagonism of the Foliar Uptake of Glyphosate into Grasses by Organosilicone Surfacants. Part 2: Effects of Surfacant Structure and Glycerol Addition", Pest.ic. Sci. 1993, 38, pp. 193–200.
Peter J.G. Stevens, Organosilicone Surfactants as Adjuvants for Agrochemicals, Pestic. Sci. 1993, 38, pp. 103–122.

* cited by examiner

*Primary Examiner*—S. Mark Clardy
(74) *Attorney, Agent, or Firm*—Frommer Lawrence & Haug LLP

(57) ABSTRACT

This invention provides for, inter alia, a method for increasing the rainfastness of an agrochemical composition without increasing its spreading properties, which comprises adding to said agrochemical composition an effective amount of one or more silicone surfactants of the formula $$R_3Si-O-[RR'SiO-]_n-O-SiR_3$$

wherein n is 1 to 3,

R is an alkyl radical with 1 to 6 carbon atoms,

R' is a radical of the structure $$-(CH_2)_m-O-(C_2H_4O)_y(C_2H_3R''O)_z-Z,$$

wherein m is 2 to 6,

R" is independantly methyl, ethyl or phenyl,

Z is hydrogen, an alkyl radical with 1 to 4 carbon atoms, or an acyl radical with 2 to 6 carbon atoms, y is 6 to 30, z is 0 to 10, with the proviso that the ratio y/z is 1 or greater, and that the total number of alkylene oxide groups $n*(y+z)$ in the siloxane polymer (I) is at least 12.

41 Claims, No Drawings

USE OF NON-SPREADING SILICONE SURFACTANTS IN AGROCHEMICAL COMPOSITIONS

BACKGROUND OF THE INVENTION

1. Field of the Invention

The invention relates to a method of improving the performance of agricultural compositions particularly with respect to rainfastness, run-off properties and efficacy under conditions of low humidity, by using silicone surfactants that reduce the surface tension to less than about 30 mN/m in 0.10% (w/w) aqueous solution thereof without concomitant spreading of the spray solution.

2. Description of the Related Art

Foliar-applied pesticidal and plant growth modifying chemicals are widely used in agricultural, industrial, recreational and residential areas worldwide. These chemical agents illustratively include insecticides, fungicides, herbicides, plant growth regulators and plant nutrients among other chemicals. Such chemicals are typically applied by spraying on the foliage of vegetation to be protected, controlled, killed or modified, but other methods such as rope-wick application are known. Some of these agents show contact action, killing, controlling or modifying the growth of target organisms at the site of deposition. Other chemicals are systemic, translocating within the plant to a site of action remote from the site of deposition. Still other chemicals show both contact and systemic action.

Surfactant formulations are commonly used in forestry, agriculture, and horticulture as agricultural adjuvants to improve the efficacy of agrochemical active ingredients such as micronutrients, growth regulators, biologicals, pesticides such as herbicides, fungicides, insecticides, acaracides and miticides. Surfactants are often used as dispersants, wetting and spreading agents, and emulsifiers in a formulated product or package or in a tank mix. Prior art identifies spreading of spray solution on the weed leaf as an essential criterion for surfactant efficacy. Surfactants have been used to improve herbicide performance since organic herbicides were first developed in the 1940s. Spreading the spray solution on weed leaves has always been a major reason for the inclusion of surfactants. This is clearly expressed in the preface to "Adjuvants for Herbicides" Weed Science Society of America Monograph Series Number 1, 1988, R. H. Hodgson (ed). It includes the statement "Experience shows that successful weed control often depends on the appropriate use of adjuvants in herbicide sprays to ensure uniform application and target coverage".

Herbicides commonly have been formulated with surfactants. Organosilicone surfactants provide surface tension values significantly lower than other commonly used surfactants. For example, the use of an organosilicone surfactant such as BREAK-THRU® S240, Goldschmidt Chemical Corp., or Silwet® L-77, Crompton Corp., in combination with a pesticide results in increased foliar uptake of the pesticide and, hence, increased efficacy of the pesticide in control of weed growth.

Among the numerous studies of the foliar uptake of the herbicide glyphosate combined with such silicone surfactants are those reported by Field & Bishop in Pesticide Science, 1988, Vol. 24, pp. 55–62; Stevens et al. in Pesticide Science, 1991, Vol. 33, pp. 371–82; Gaskin & Stevens in Pesticide Science. 1993, Vol. 38, pp. 185–92; and Gaskin & Stevens in Pesticide Science, 1993. Vol. 38, pp. 193–200. An extensive review of 160 references relating to the use of organosilicones as adjuvants for agrochemicals was provided by Stevens in Pesticide Science, 1993, Vol. 38, pp. 103–22. It is well recognized in the art that trisiloxane ethoxylate surfactants with no more than about 10 ethylene oxide units have the ability to impart the property of superspreading to agricultural spray mixtures. The term "superspreading" means the ability of a drop of the mixture to spread to a diameter at least 9 times as great as a drop of distilled water on a hydrophobic surface such as the leaf of a plant.

The fact that superspreading has been considered an essential attribute of such silicone surfactants is confirmed by the fact that various patents have been issued with improved spreading as the main objective. For example, U.S. Pat. No. 5,104,647 to Policello and U.S. Pat. No. 5,558,806 to Policello and Murphy have as main objective maintaining the superspreading capability of organosilicone/organic surfactant blends.

U.S. Pat. No. 5,017,216 to Dow Corning discloses postemergent herbicide compositions containing silicone glycol adjuvants, comprising blends of trisiloxane surfactants of the structure $Me_3SiO$—$SiMeR'$—$O$—$SiMe_3$ wherein R' is a short-chain polyether radical with typically 4.6 ethylene oxide units, in combination with siloxane dispersants.

WO 89/12394, WO 99/40785, U.S. Pat. No. 6,051,533, U.S. Pat. No. 6,040,272 and EP 0483095, all to Monsanto, disclose various herbicide compositions comprising silicone surfactants in combination with other adjuvants like humectants, oils, glycol esters and organic cosurfactants. For the silicone surfactants claimed to be useful in these inventions, the inventors disclose a very broad structural range and provide little direction to those skilled in the art about which of these siloxane surfactants are to be advantageously used to enhance the efficacy of herbicide compositions. However, the examples used in these inventions are trisiloxanes like Silwet® L77 or Silwet® 408, having typical structures like $Me_3SiO$—$SiMeR'$—$O$—$SiMe_3$ wherein R' a radical —$(CH_2)_3$—$(CH_2CH_2O$—$)_8$—Z wherein Z is hydrogen or methyl. It is well known to a person skilled in the art that trisiloxane surfactants of that type convey superspreading properties to aqueous solutions thereof, as long as the polyether chain length does not exceed about 10 ethylene oxide units. The fact that only such superspreading siloxanes have been chosen to exemplify the invention shows that the inventors were following the common belief that enhanced spreading is an essential attribute for silicone surfactants to be useful as adjuvants in herbicide compositions for most applications.

It is equally well-known to the practitioner of the art that silicone surfactants can have antagonistic effects on the efficacy on herbicides on certain plant species. Gaskin, et al., (Pestic. Sci. 1993, 38, 185–192) demonstrated that some trisiloxane ethoxylates (TSE), such as Silwet® L-77 surfactant (available from Crompton), can antagonize cuticular penetration of a herbicide into grasses, when compared to the herbicide alone. The term antagonism is used to indicate that the treatment of herbicide plus adjuvant is less effective than the comparative herbicide treatment. This tendency to antagonize the activity of glyphosate on some species in the absence of rain can be mitigated by the addition of a humectant such as glycerin to the spray solution, as disclosed in WO 89/12394. This addition prevents rapid drying of the spray solution which commonly is experienced when using superspreading silicone surfactants under conditions of low humidity, such as, for example, a relative humidity of 30% or less.

Gaskin, et al., (Pest. Sci. 1993, 38, 192–200) also studied the antagonism of glyphosate by trisiloxane surfactants with 8 to 40 ethylene oxide units and found that the antagonism is reduced when using surfactants with increased ethylene oxide content. However, no information was provided on rainfastness, and run-off behaviour of the glyphosate compositions, or on efficacy under conditions of low humidity.

It is also common knowledge that surfactants with high content of ethylene oxide groups usually have melting points above common use temperatures and thus are impractical to handle during application. Therefore it is usually desirable to use adjuvants which are liquid at room temperature.

Great Britain Pat. No. 1,255,249 to Dow Corning Corporation, published Dec. 1, 1971, discloses herbicide compositions employing silicone glycol copolymers. Here, general utility of a large number of adjuvants is professed, as exemplified by two generic silicone glycol formulas which embrace structures having both diorganosiloxane units and alkyl-glycol siloxane units. There are also provided two examples employing a triazine herbicide in conjunction with an adjuvant having 1.8 siloxy units and bearing a glycol chain consisting exclusively of 12 ethylene oxide units showing enhanced efficacy of the herbicide. However, no information is disclosed on rainfastness, and run-off behaviour of the herbicide composition, or on efficacy under conditions of low humidity. In addition, it is well known to the practioner of the art that such surfactants with a large number of only ethylene oxide units are solid at low use temperatures, such as 45 to 50 F., and thus impractical to handle.

It has now surprisingly been found that the use of silicone surfactants which reduce the surface tension in 0.1% (w/w) aqueous solution to less than about 30 mN/m without increasing the spreading properties results in a significantly improved performance of agrochemical compositions, such as herbicide compositions. The use of said siloxanes can improve, for example, the rainfastness, run-off, efficacy under conditions of low humidity without the need for additional humectants, and they can even be used in combination with cosurfactants which have an adverse effect on the spreading properties of superspreading silicone surfactants, and therefore offer a wider latitude of formulations.

It has further been found that silicone surfactants which are liquid at use temperature and reduce the surface tension in 0.10% (w/w) aqueous solution to less than about 30 mN/m without increasing the spreading properties thereof can especially advantageously be used to enhance the performance of agrochemical compositions, such as herbicide compositions. The use of said siloxanes can improve the efficacy, rainfastness, run-off, performance under conditions of low humidity without the need for additional humectants, and they can also be used in combination with cosurfactants which have an adverse effect on the spreading properties of superspreading silicone surfactants.

OBJECTS OF THE INVENTION

It is an object of this invention to provide a method for enhancing the performance of agrochemical compositions with respect to rainfastness, run-off, efficacy under conditions of low humidity without the need for additional humectants, by using silicone surfactants capable of reducing the surface tension of 0.10% (w/w) aqueous solutions thereof to less than about 30 mN/m without enhancing the spreading properties. It is a further object to provide a method for enhancing the performance of agrochemical compositions with respect to efficacy, rainfastness, run-off, efficacy under conditions of low humidity without the need for additional humectants, by using silicone surfactants which are liquid at use temperature and capable of reducing the surface tension of 0.10% aqueous solutions thereof to less than about 30 mN/m without enhancing the spreading properties.

DETAILED DESCRIPTION OF THE INVENTION

Silicone surfactants which can be used within the scope of this invention, are polysiloxane-based surfactants containing polyether groups having such structural features that they are capable of reducing the static surface tension of a 0.10% (w/w) aqueous solution of the silicone surfactant to less than about 30 mN/m without enhancing the spreading properties thereof. In this invention, a silicone surfactant surfactant is defined as "not enhancing the spreading properties of a 0.10% aqueous solution thereof" or as a 'non-spreading silicone surfactant' if the spreading area of a 0.10% (w/w) aqueous solution of said silicone surfactant on a polypropylene test substrate is reduced by a factor of about 10 or more, compared to a conventional super-spreading silicone surfactant such as Silwet® L-77 or Breakthru® S240, which is well known to the practitioner of the art as a typical super-spreading surfactant.

Preferred silicone surfactants capable of reducing the static surface tension of a 0.10% (w/w) aqueous solution of the silicone surfactant to less than about 30 mN/m without enhancing the spreading properties have the general structure:

$$R_3Si-O-[RR'Si-O-]_n-O-SiR_3 \qquad (I),$$

wherein
n is 1 to 3,
R is an alkyl radical with 1 to 6 carbon atoms,
R' is a radical of the structure $$-(CH_2)_m-O-(C_2H_4O)_y(C_2H_3R''O)_z-Z,$$

wherein
m is 2 to 6,
R" is independantly methyl, ethyl or phenyl,
Z is hydrogen, an alkyl radical with 1 to 4 carbon atoms, or an acyl radical with 2 to 6 carbon atoms,
y is 6 to 30, and
z is 0 to 10,
with the proviso that the ratio y/z is 1 or greater, and that the total number of alkylene oxide groups $n*(y+z)$ in the siloxane polymer (I) is at least 12.

Preferred alkyl radicals for R and R" are methyl, a preferred value for m is 3.

A preferred subclass (a) are silicone surfactants (I), wherein
n is 1, R and R" is methyl, m is 3, y is 13 to 30, z is 0 to 2, especially preferred 0, and Z is hydrogen, methyl or acetyl.

Another preferred subclass (b) are silicone surfactants (I), wherein
n is 2, R and R" is methyl, m is 3, y is 6 to 20, z is 0 to 2, especially preferred 0, and Z is hydrogen, methyl or acetyl.

Another preferred subclass (c) are silicone surfactants (I), wherein
n is 1, R and R" is methyl, m is 3, y is 8 to 30, z is 2 to 10, and Z is hydrogen, methyl or acetyl, and the ratio y/z is 2 to 10 (i.e., 2:1 to 10:1), especially preferred 2 to 6.

Another preferred subclass (d) are silicone surfactants (I), wherein n is 2, R and R" is methyl, m is 3, y is 5 to 20, z is 1 to 6 and Z is hydrogen, methyl or acetyl and the ratio y/z is 2 to 10, especially preferred 2 to 6.

Further preferred are any mixtures of two or more of the preferred subclasses (a to d).

Surfactants of subclass (c) and (d) have the additional benefit that the presence of propylene oxide units tends to reduce the melting point of the silicone surfactants, compared to materials containing only ethylene oxide units, resulting in materials with the desirable property of being liquid even at low use temperature such as 45 to 50° F. so they are easy to handle during application.

Illustrative examples of siloxanes showing the required physical properties are shown below. These structures are given as typical examples, without intending to limit the scope of the invention:

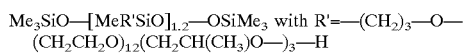

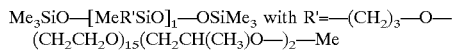

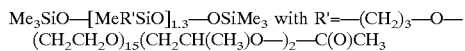

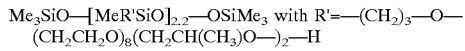

It is well known to the practioner of the art, that the polyalkyleneoxide polymers have a broad molecular weight distribution and that the indices stated above designate the average composition only. The distribution of the different alkylene oxide units can be random or in blocks.

The siloxane surfactants described above can be prepared by methods well known to the practioner of the art, such as, for example, by hydrosilylation reaction of a Si—H containing siloxane and an unsaturated polyoxyalkylene derivatives, such as an allyl derivative, in the presence of a platinum catalyst. The reaction conditions and catalysts employed have been described in detail, for example, by W. Noll in "Chemie und Technologie der Silicone", 2nd ed., Verlag Chemie, Weinheim (1968), by B. Marciniec in "Appl. Homogeneous Catal. Organomet. Compd.1996, 1, 487)" or by G. C. Davis et al. in U.S. Pat. No. 5,204,438. It is common knowledge in the art that the hydrosilylation products of SiH-containing siloxanes with unsaturated polyoxyalkylene derivatives may contain excess unsaturated polyoxyalkylene derivative, or an isomerization product thereof. It is equally well understood that the linear siloxane derivatives, and the mixtures thereof, may contain up to 10%, preferred less than 5%, of cyclic siloxanes.

The siloxane surfactants described above may further be modified by introduction of units of the type

wherein R has the meaning as stated above, R" is a linear or branched alkyl radical with 6 to 30 carbon atoms which may be additionally substituted by nitrogen atoms. Preferred radicals R" are alkyl groups with 10 to 18 carbon atoms, aminopropyl and dimethylaminopropyl. Modified siloxane surfactants can be prepared by methods well-known to the practitioner of the art, for example by equilibration of siloxanes (I) with linear or cyclic siloxanes or mono- or di-alkoxysilanes containing the units —[RR"Si—O—], in the presence of an equilibration catalyst such as, for example, a hydroxide, or alkoxide of sodium, potassium or tetraalkylammonium, or by equilibration of the precursor SiH-containing siloxanes with siloxanes or alkoxysilanes containing the units —[RR"Si—O—] in the presence of an acid or base catalyst, followed by hydrosilylation with an unsaturated polyoxyalkylene compound.

The use of the non-spreading silicone surfactants described above provides a method for enhancing the efficacy and rainfastness of agrochemical compositions in general and for reducing run-off from the plant which is commonly experienced when using superspreading silicone surfactants. They may be used to enhance the efficacy of agrochemical compositions under adverse conditions such as low humidity without the need for further humectants. If the non-spreading silicone surfactants contain significant amounts of propylene oxide units in their polyoxyalkylene side chain, the user has the additional benefit of having adjuvants which are liquid at low use temperature and thus easy to handle, without the need for solvents or additional premixing/dissolving.

The non-spreading silicone surfactants of this invention can be advantageously used with a variety of agrochemical compositions, such as compositions comprising micronutrients, growth regulators, pesticides such as herbicides, fungicides, insecticides, acaracides and miticides. Especially advantageous is the use in compositions comprising herbicides. Suitable herbicides are, for example: Growth regulators such as:

Phenoxy Acetic Acids, such as 2,4-D [(2,4-dichlorophenoxy)acetic acid];
Phenoxy Propionic Acids, such as Dichlorprop[(RS)-2-(2, 4-dichlorophenoxy) propionic acid], Mecoprop [(RS)-2-(4-chloro-o-tolyloxy)-propionic acid];
Phenoxy Butyric Acids, such as 2,4-DB[4-(2,4-Dichlorophenoxy)butyric acid];
Benzoic Acids, such as Dicamba [3,6-dichloro-o-anisic];
Other growth regulators, such as Fluroxypyr [4-amino-3,5-dichloro-6-fluoro-2-pyridyloxy-acetic acid], Picloram [4-amino-2,3,5-trichlor-2-carboxylic acid], Triclopyr [3,5,6-trichloro-2-pyridyloxyacetic acid], Copyralid [3,6-dichloropyridine-2-carboxylic acid];
Pigment Inhibitors: such as Amitrole, [1H-1,2,4-triazol-3-ylamine; 3-amino-1H-1,2,4triazole], Clomazone [2-(2-chlorobenzyl)-4,4-dimethyl-1,2-oxazolidin-3-one;2-(2-chlorobenzyl)-4,4-imethylisoxazolidin-3-one], Fluridone [1-methyl-3-phenyl-5-(a,a,a-trifluoro-m-tolyl)4-pyridone], Norflurazone [4-chloro-5-methylamino-2-(a,a, a-trifluoro-m-tolyl)pyridazin-3(2H)-one];
Mitotic disruptors, for example: Dinitroanilines, such as Isopropalin [4-isopropyl-2,6-dinitro-N,N-dipropylaniline], Oryzalin [3,5-dinitro-N4N4-dipropylsulfanilamide], Pendimethalin [N-(1-ethylpropyl)-2,6-dinitro-3,4-xylidine], Prodiamine [5-dipropylamino-a,a,a-trifluoro-4,6-dinitro-toluidine; 2,6-dinitro-N1N1-dipropyl-4-trifluoromethyl-m-phenylenediamine], Trifluralin [a,a,a-trifluoro-2,6-dinitro-N,N-dipropyl-p-toluidine];
Inhibitors of lipid biosynthesis, such as Clethodim [(±)-2-[(E)-3-chloroallyloxyimino]propyl]-5[2(ethylthio)-propyl]-3-hydroxycyclohex-3-enone], Diclofop-methyl [(RS)-2-[4-(2,4-dichlorophenoxy)phenoxy]propionic acid], Fenoxaprop-ethyl [(±)-2-[4-(6-chloro-1,3- benzoxazol-2-yloxy)phenoxy]propionic acid; (±)-2-[4-(5-chlorobenzoxazol-2-yloxy)phenoxy]propionic acid], Fluazifop-P-butyl [(R)-2-[4-(5-trifluoromethyl-2-pyridyloxy)phenoxy)propionic acid, Haloxyfop-methyl [(RS)-2-(4-(3-chloro-5-trifluoromethyl 2-pyridyloxy) phenoxy]propionic acid], Quizalofop[.(RS)-2[4-(6-chloroquinoxalin-2-yloxy)phenoxy]propionic acid], Sethoxydim[.(±)-(EZ)-2-(1-ethoxyininobutyl)-5-[2 (ethylthio)propyl]-3-hydroxycyclohex-2-enone];

Photosynthesis Inhibitors:

Triazines and s-Triazines such as Hexazinone [3-cyclohexyl-6-dimethylamino-1-methyl-1,3,4-triazine-2,4(1H,3H)-dione], Metribuzin [4-amino-6-tert-butyl-3-methylthio-1,2,3-triazine-5(4H)-one], Atrazine [6-chloro-N2-ethyl-N4-isopropyl-1,3,5-triazine-2,4-diamine], Simazine [6-chloro-$N^2$,$N^4$-diethyl-1,3,5-triazine-2,4-diamine], Cyanazine 2-[4-chloro-6-ethylamino-1,3,5-triazin-2-yl]amino]-2-methylpropanenitrile, Prometon [$N^2$,$N^2$4-di-isopropyl-6-methoxy-1,3,5-triazine-2,4,diamine], Ametryn [$N^2$-ethyl-$N^4$-isopropyl-6-methylthio-1,3,5-triazine-2,4-diamine];

Substituted ureas, such as Diuron [3-(3,4-dichlorophenyl)-1,1-dimethylurea], Fluometuron [1,1-dimethyl-3-(a,a,a-trifluoro-m-tolyl) urea], Linuron [3-(3,4-dichlorophenyl)-1-methoxy-1-methylurea], Tebuthiuron [1-(5-tert-butyl,1,3,4-thiadiazol-2-yl)-1,3-dimethylurea], Uracils, such as Bromacil [5-bromo-3-sec-butyl-6-methyluracil], Terbacil [3-tert-butyl-5-chloro-6-methlyuracil];

Other photosynthesis inhibitors, such as Bentazon [3-isopropyl-1H-2,1,3-benzothiadiazin-4(3H)-one 2,2-dioxide], Desmedipham [ethyl 3'-phenylcarbamoyloxycarbanilate; ethyl 3-phenylcarbamoyloxyphenylcarbamate; 3-ethoxycarbonylaminophenyl phenylcarbamate], Methazole [2-(3,4-dichlorophenyl)-4-methyl-1,2,4-oxadiazolidine-3,5-dione], Phenmedipham [methyl 3-(3-methylcarbaniloyloxy) carbanilate, 3-methoxycarbonylaminophenyl 3'-methylcarbanilate], Propanil [3',4'-dichloropropionanilide], Pyridate [6-chloro-3-phenylpyridazin-4-yl S-octyl thiocarbonate];

Inhibitors of amino acid synthesis, such as Glyphosate, Sulfosate and other salts of N-(phosphonomethyl)glycine;

Sulfonylureas, such as Bensulfuron [a-(4,6-dimethoxypyrimidin-2-ylcarbamoylsulfamoyl)-o-toluic acid], Chlorimuron [2-(4-chloro-6-methoxypyrimidin-2-ylcarbamoylsulfamoyl)benzoic acid], Chlorsulfuron [1-(2-chlorophenylsulfonyl)-3-(4-methoxy-6-methyl-1,3,5-triazin-2-yl) urea], Metsulfuron [2-(4-methoxy-6-methyl-1,3,5-triazin-2-ylcarbamoylsulfamoyl)benzoic acid], Nicosulfuron [2-(4,6-dimethoxypyrimidin-2-ylcarbamoylsulfamoyl)-N,N-dimethylnicotinamide; 1-(4,6-dimethoxypyrimidin-yl)-3-(3-dimethylcarbamoyl-2-pyridylsulfonyl)urea], Primisulfuron [2-(4,6-bis (difluoromethoxy)pyrimidin-2-ylcarbamoylsulfamoyl) benzoic acid], Sulfometuron [2-(4,6-dimethylpyrimidin-2-ylcarbamoylsulfamoyl)benzoic acid; 2-[3-(4,6-dimethylpyrimidin-2yl)ureidosulfonyl)]benzoic acid], Thifensulfuron [3-(4-kethoxy-6-methyl-1,3,5-triazin-2ylcarbamoylsulfamoyl)thiophen-2-carboxylic acid], Triasulfuron [1-(2-(2-chloroethoxy)phenylsulfonyl)-3(4-methoxy-6-methyl-1,3,5-triazin-2yl)urea], Tribenuron [2-(4-methoxy-6-methyl-1,3,5-triazin-2-yl(methyl) carbamoylsulfamoyl)benzoic acid];

Imidazolinones, such as Imazamethabenz [a reaction product comprising(±)-6-(4-isopropyl-4-methyl-5-oxo-2-imidazolin-2-yl)-m-toluic acid and (±)-2-(4-isopropyl-4methyl-5-oxo-2-imidazolin-2-yl)-p-toluic acid], Imazapyr [2-(4-isopropyl-4-methyl-5-oxo-2-imidazolin-2yl)nicotinic acid], Imazaquin [(RS)-2-(4-isopropyl-4-methyl-5-oxo-2-imidazolin-2-yl)quinoline-3-carboxylic acid], Imazethapyr [(RS)-5-ethyl-2-(4-isopropyl-4-methyl-5-oxo2-imidazolin-2-yl)nicotinic acid];

Cell membrane disruptors: Bipyridylium compounds, such as Diquat [9,10-dihydro-8a-diazoniaphenanthrene; 6,7-dihydrodipyrido[1,2-a:2',1'-c]pyrazine-5,8-dium; 1,1'-ethylene-2,2'-bipyridyldiylium], Paraquat [1,1'-dimethyl-4,4'-bipyridinium(I)], Diphenylethers, such as Acifluorfen [5-(2-chloro-a,a,a-trifluro-p-tolyoxy)-2-nitrobenzoic acid], Fomesafen [5-(2-chloro-a,a,a-trifluro-p-tolyloxy)-N-mesyl-2-nitrobenzamide; 5-(2-chloro-a,a,a-trifluoro-p-tolyoxy)-N-methylsulfonyl-2-nitrobenzamide], commercially available as REFLEX®, Lactofen [ethyl 0-(5-(2-chloro-a,a,a-trifluoro-p-tolyl-oxy)-2-nitrobenzoyl)-DL-lactate], Oxyfluorfen [2-chloro-a,a,a-trifluoro-p-tolyl 3-ethoxy-4-nitrophenyl ether];

Cell wall inhibitors like Dichlobenil [2,6-dichlorobenzonitrile], Isoxaben [N-[3-(1-ethyl-1-methylpropyl)-1,2-oxazol-5-yl]-2,6-dimethoxybenzamide; N[(3-(1-ethyl-1-methylpropyl) isoxazol-5-yl]-2,6-dimethoxybenzamide];

Other herbicides such as Glufosinate [4-(hydroxy(methyl) phosphinoyl]-DL-homoalaine; DL-homoalanin-4-yl-(methyl)phosphinic acid], Bromoxynil, [3,5-dibromo-4-hydroxybenzonitrile]; 3,5-dibromo-4-hydroxyphenyl cyanide, 2,6-dibromo-4-cyanophenyl octanoate].

Aryltriazoliones such as carfentrazone-ethyl.

Especially preferred herbicides are N-(phosphonomethyl) glycine and its salts.

It is understood by those skilled in the art that the use of co-surfactants and co-adjuvants is common practice in spray tank mixes, pesticide formulations and within adjuvant blends. Therefore the scope of this patent is understood to include the use of the present invention in combination with other adjuvants, including but not limited to, surfactants, stickers, humectants, solvents, oils, drift control agents, buffers, extenders, deposition and retention aids, defoamers and antifoams, compatibility agents, and herbicide activity enhancers such as ammonium sulfate and nitrogen-containing fertilizers. Blends of other surfactants with these novel siloxanes is especially beneficial when a variety of properties may be desired from the adjuvant. Co-surfactants can include nonionic, cationic, anionic, and zwitterionic surfactants. Examples of potential co-surfactants include, but are not limited to the following: alkanolamides, alkyl aryl alkoxylates and their derivatives, alkoxylated amines and their derivatives, quaternary ammonium surfactants, alkoxylated quaternary ammonium surfactants and their derivatives, amine oxides, betaines and their derivatives, copolymers containing ethylene oxide, propylene oxide, butylene oxide, styrene oxide or any combination thereof, linear alcohol alkoxylates and their derivatives, branched alcohol alkoxylates and their derivatives, alkoxylated amides, alkoxylated fatty acids, alkoxylated fatty esters and oils, glycerol esters, alkoxylated glycerol esters, imidazolines and their derivatives, propoxylated quaternary amines, lignin and its derivatives (such as lignosulfonate salts), mono- and di-glycerides, olefin sulfonates, phosphate esters, alkyl polyglycosides, other siloxane surfactants (such as alkoxylated siloxanes, alkyl siloxanes, siloxanes containing betaine and quaternary ammonium groups, amino siloxanes, and alkoxylated amino siloxanes), sorbitan esters, ethoxylated sorbitan esters, sulfonate surfactants, sulfosuccinates and their derivatives, salts of fatty acids, and sarcosinates. By definition, the term 'fatty' as used in this invention includes materials of animal and plant origin.

In addition to being useful with the surfactants having no adverse effects on the spreading properties of herbicide compositions containing superspreading silicone surfactants, which are disclosed in U.S. Pat. Nos. 5,558,806 and 5,104,647 and are herein included by reference, the non-spreading siloxanes of the present invention can also be advantageously blended with surfactants that are known to antagonize super-spreading siloxanes. Examples of these include, but are not limited to: ethoxylated alkyl amines (such as Varonic® surfactants produced by Goldschmidt Chemical Corporation), ethoxylated alkyl quaternary ammonium surfactants, propoxylated quaternary ammonium surfactants (such as the Variquat® surfactants produced by Goldschmidt Chemical Corporation), ethoxylated alkyl aryl alcohols and their derivatives, linear and branched alcohol ethoxylates. By definition, the term alkyl as used in this patent can refer to both saturated and unsaturated hydrocarbon chains.

The method of this invention can be used for liquid and solid agrochemical compositions. They can be used in spray tank mixes, pesticide formulations, adjuvant blends, and in applications where the silicone surfactant is administered in a sequential addition after the application of the herbicide, such as disclosed in U.S. Pat. Nos. 5,985,793 and 5,821,195 which are incorporated herein by reference. Typical use temperatures are about 45° F. to 100° F.

Typical agrochemical formulations comprising non-spreading siloxanes and effective amounts of active ingredients can comprise, for example, 1 to 50% of siloxane(s), preferably 2 to 20% siloxane by weight of the total formulation.

If containing additional co-surfactants, typical adjuvant formulations comprising non-spreading siloxanes can comprise, about 1 to about 99% by weight of siloxane(s) and 0 to about 99% of co-surfactant(s), preferred about 10 to about 70% by weight of siloxane(s) and 30 to 90% of co-surfactant(s), especially preferred about 25 to about 50% siloxane(s) and about 50 to about 75% co-surfactant(s).

EXAMPLES

Spread Test

Spread areas of the various solutions were determined by applying 50 microliters of 0.10% (w/w) aqueous surfactant solution to a standard polypropylene film (Type: Forco-OPPB, translucent, made by Van Leer) using a micropipette. Solution spread diameters were measured and the areas calculated 90 seconds after application. Deionized water was used for all testing and the ambient relative humidity was maintained at a minimum of 40%.

Surface Tension

All surface tension values were measured by the Wilhelmy plate method using a Kruss K 12 tensiometer.

Materials

Silwet® L-77 and Silwet® 806 are commercial superspreading trisiloxane surfactants, available from Crompton Corp, White Plains, N.J.

Break-Thru® S240 and Break-Thru® S278 are commercial superspreading trisiloxane surfactants, available from Goldschmidt Chemical Corporation, Hopewell, Va.

Sylgard® 309 is a commercial superspreading trisiloxane surfactant, available from Dow Corning, Midland, Mich.

Silicone surfactant A is a non-spreading silicone surfactant having a structure

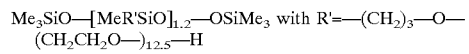
$Me_3SiO-[MeR'SiO]_{1.2}-OSiMe_3$ with $R'=-(CH_2)_3-O-(CH_2CH_2O-)_{12.5}-H$ Silicone surfactant B is a non-spreading silicone surfactant having a structure

$Me_3SiO-[MeR'SiO]_{1.2}-OSiMe_3$ with $R'=-(CH_2)_3-O-(CH_2CH_2O-)_{10}(CH_2CH(CH_3)O-)_2-H$ Silicone surfactant C is a non-spreading silicone surfactant having a structure

$Me_3SiO-[MeR'SiO]-OSiMe_3$ with $R'=-(CH_2)_3-O-(CH_2CH_2O-)_{20}(CH_2CH(CH_3)O-)_5-H$ Silicone surfactant D is a non-spreading silicone surfactant having a structure

$Me_3SiO-[MeR'SiO]-OSiMe_3$ with $R'=-(CH_2)_3-O-(CH_2CH_2O-)_{12.5}-H$ Silicone surfactant E is a non-spreading silicone surfactant having a structure

$Me_3SiO-[MeR'SiO]_{1.2}-OSiMe_3$ with $R'=-(CH_2)_3-O-(CH_2CH_2O-)_{12.5}-Me$ Silicone surfactant F is a non-spreading silicone surfactant having a structure

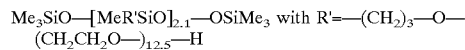
$Me_3SiO-[MeR'SiO]_{2.1}-OSiMe_3$ with $R'=-(CH_2)_3-O-(CH_2CH_2O-)_{12.5}-H$ Silicone surfactant G is a non-spreading silicone surfactant having a structure

$Me_3SiO-[MeR'SiO]-OSiMe_3$ with $R'=-(CH_2)_3-O-(CH_2CH_2O-)_{17}-H.$ The following commercial herbicides were used in the field studies:

| Commercial Herbicide | Common Chemical Name | Manufacturer |
| --- | --- | --- |
| Roundup ® | Glyphosate | Monsanto |
| Sempra ® | Halosulfuron-methyl | Monsanto |
| 2,4-D AMINE Weed Killer ® | 2,4 D | Universal Cooperatives, Inc. |
| Ally ® | Metsulfuron-methyl | DuPont |
| Pursuit ® | Imazethapyr | BASF |

TABLE 1

Comparison of Physical Chemical Properties New Organosilicone Herbicide Adjuvants Compared with the Existing Commercial Adjuvants

| Compound | Static Surface Tension (Dynes/cm) | Spread (cm$^2$) | at 50° F. | at 60° F. | at 70° F. |
|---|---|---|---|---|---|
| Silwet ® L77* | 23.8 | 61.0 | liquid | liquid | liquid |
| Silwet ® 806* | 23.6 | 54.3 | liquid | liquid | liquid |
| Break-Thru ® S240* | 22.4 | 53.3 | liquid | liquid | liquid |
| Break-Thru ® S278* | 22.0 | 54.1 | liquid | liquid | liquid |
| Sylgard ® 309* | 23.5 | 58.5 | liquid | liquid | liquid |
| silicone surfactant A | 25.1 | 1.2 | solid | solid | liquid |
| silicone surfactant B | 24.2 | 1.6 | liquid | liquid | liquid |
| silicone surfactant C | 28.2 | 0.7 | liquid | liquid | liquid |
| silicone surfactant D | 23.8 | 1.4 | solid | solid | liquid |
| silicone surfactant E | 25.0 | 1.3 | solid | solid | solid |
| silicone surfactant F | 29.8 | 0.7 | solid | solid | liquid |
| silicone surfactant G | 29.5 | 0.9 | solid | solid | solid |

All data for 0.1% v/v solutions
*commercial superspreading trisiloxane surfactant In the spreading test, typical superspreading silicone surfactants show a spread area of 40 cm$^2$ or more, while the non-spreading silicone surfactants of this invention show a spreading area of 4 cm$^2$ or less. Surfactants B and C are non-spreading silicone surfactants which are liquid at use temperatures of 50 F. and higher.

Example 1

Rainfastness on Broadleaf Weeds with the Herbicide Glyphosate

It is commonly accepted that rainfall up to six hours after treatment with the commercial herbicide Roundup reduces weed control. A field trial was conducted to evaluate the performance of two non-spreading silicone adjuvants A and B, with Roundup® (active ingredient is the isopropylamine salt of n-phosphonomethyl glycine), on broadleaf weeds when rain falls shortly after application. The weeds were specially grown for the study. Seeds of common purslane (*Portulaca oleracea*) were broadcast over the experimental area and incorporated with a field cultivator/harrow. The experimental design was a randomized complete block with three replications of paired plots (simulated rain and no rain) for each herbicide and adjuvant combination. The applications were made with a backpack sprayer delivering 20 gal/acre. Simulated rainfall was applied 60 minutes after herbicide treatments using a tractor mounted sprayer delivering 2139 gal/acre (2 mm rainfall). Herbicide performance was evaluated visually 21 days after treatment by a skilled field experimenter.

| Herbicide (Rate) | Tank Mix Adjuvant | % Control (Kill) of Common Purslane | |
|---|---|---|---|
| | | No Rain | Rain |
| Roundup ® (12 oz/acre) | None | 53 | 12 |
| Roundup ® (12 oz/acre) | SILICONE SURFACTANT A | 55 | 37 |
| Roundup ® (12 oz/acre) | SILICONE SURFACTANT B | 62 | 28 |
| Roundup ® (24 oz/acre) | None | 82 | 25 |
| Roundup ® (24 oz/acre) | SILICONE SURFACTANT A | 82 | 55 |
| Roundup ® (24 oz/acre) | SILICONE SURFACTANT B | 87 | 50 |

All adjuvant rates were 0.1% v/v of the spray solution.

Both silicone surfactants provided rainfastness to Roundup. The addition of each to the spray solution more than doubled weed control compared to Roundup alone when the plots were subjected to 2 mm of simulated rain 60 minutes after herbicide application.

Example 2

Rainfastness on Grassy Weeds with the Herbicide Glyphosate

A natural infestation of the perennial grass, *Bracharia decumbens*, was sprayed with the commercial herbicide Roundup, (active ingredient: isopropylamine salt of n-phosphonomethyl glycine), alone or with an adjuvant included in the spray solution. The spray volume was 200 liter/ha. Sixty minutes after the herbicide application half of each experimental plot received 2 mm of simulated rain. Herbicide performance was evaluated visually 30 days after treatment by a skilled field experimenter.

| Herbicide Rate | Tank Mix Adjuvant | % Grass Control | |
|---|---|---|---|
| | | No Rain | Rain |
| Roundup ® 2.4 1/ha | None | 65 | 22 |
| Roundup ® 2.4 1/ha | Break-Thru ® S240 | 70 | 32 |
| Roundup ® 2.4 1/ha | SILICONE SURFACTANT B | 77 | 38 |

All adjuvant rates were 0.1% v/v of the spray solution.

SILICONE SURFACTANT B enhanced the Roundup rainfastness. It also improved the efficacy of Roundup in the absence of rain. The grass control with SILICONE SURFACTANT B was higher than with the commercial super spreading silicone surfactant, Break-Thru® S240.

Example 3
Rainfastness with Sulfonyl Urea Herbicides

A small plot field trial was conducted to determine the rainfastness performance of a non-spreading trisiloxane tank mix adjuvant compared to a super-spreading commercial silicone (Break-Thru® S240) with the sulfonylurea herbicide, Halosulfuron. The commercial formulation of the herbicide used was Sempra. The target weeds were a naturally occurring very heavy infestation of Purple Nutsedge (*Cyperus rotundus*) with 1200 to 1400 plants per hectare. The experiment had four replications. Sempra was applied at the commercial rate (150 g/ha) and half that rate. The adjuvant rate was 0.1% v/v of the spray mix. The applications were made with a backpack sprayer with a spray volume of 200 litre/ha. At one hour after the herbicide application a simulated rain of 6 mm was applied to half of each plot with a tractor mounted sprayer. Weed control was evaluated visually by a skilled experimenter 60 days after treatment.

| HERBICIDE | TANK MIX ADJUVANT | % CONTROL *Cyperus rotundus* | |
|---|---|---|---|
| | | No Rain | Rain |
| Sempra® 75 g/ha | None | 63.3 | 38.3 |
| Sempra® 75 g/ha | Break-Thru® S240 | 73.3 | 63.3 |
| Sempra® 75 g/ha | SILICONE SURFACTANT B | 85.0 | 68.3 |
| Sempra® 150 g/ha | None | 73.3 | 63.3 |
| Sempra® 150 g/ha | Break-Thru® S240 | 91.7 | 81.7 |
| Sempra® 150 g/ha | SILICONE SURFACTANT B | 95.0 | 83.3 |

All adjuvant rates were 0.1% v/v of the spray solution.

The results demonstrate that a non-spreading siloxane adjuvant can be very effective in increasing the efficacy of a herbicide and are that they can be particularly valuable in enhancing rainfastness. In fact it generally gave better weed control than the commercial adjuvant Break-Thru® S240.

Example 4
Enhancement of Efficacy of Auxin, Sulfonylurea and Imidazalinone Herbicides A small plot field trial was conducted to evaluate the performance of silicone adjuvants with herbicides from three different chemical families. The commercial herbicides chosen were 2,4-D, Ally® and Pursuit®. The weeds were specially grown for the study. Seeds of hemp sesbania (*Sesbania exaltata*) and pitted morningglory (*Ipomea lacunosa*) were broadcast in bands over the experimental area and incorporated with a field cultivator/harrow. The weeds were large when the herbicides were applied. The experimental design was a randomized complete block with three replications. The applications were made with a backpack sprayer delivering 20 gal/acre.

Herbicide performance was evaluated visually 21 days after treatment by a skilled field experimenter.

Both adjuvants improved the performance of all three herbicides on one or other of the two species. The non-spreading silicone, SILICONE SURFACTANT B was at least as effective as the commercial super-spreading surfactant Break-Thru® S240.

| Herbicide Treatment (Rate) | Tank Mix Adjuvant | % *Ipomea lacunosa* Control | % *Sesbania exaltata* Control |
|---|---|---|---|
| 2,4 D (16 oz/a) | None | 99 | 22 |
| 2,4 D (16 oz/a) | Break-Thru® S240 | 99 | 75 |
| 2,4 D (16 oz/a) | SILICONE SURFACTANT B | 99 | 75 |
| Ally® (0.05 oz/a) | None | 65 | 15 |
| Ally® (0.05 oz/a) | Break-Thru® S240 | 65 | 87 |
| Ally® (0.05 oz/a) | SILICONE SURFACTANT B | 65 | 93 |
| Pursuit® (1.4 oz/a) | None | 45 | 0 |
| Pursuit® (1.4 oz/a) | Break-Thru® S240 | 57 | 0 |
| Pursuit® (1.4 oz/a) | SILICONE SURFACTANT B | 55 | 0 |

All adjuvant rates were 0.1% v/v of the spray solution.

Example 5
Performance of Selected Adjuvants Under Low Relative Humidity

A small plot field trial was conducted in Arizona to evaluate the performance of two silicone adjuvants, SILICONE SURFACTANTS A and B with the commercial herbicide Glyphos, active ingredient glyphosate (isopropylamine salt of n-phosphonomethyl glycine), under low relative humidity atmospheric conditions. There were four replications in the experiment. The target weeds were a naturally occurring infestations of Barnyard Grass (*Echinochloa crus-galli*) and Common Purslane (*Portulaca oleracae*). Barnyard grass is typically hard to kill with glyphosate. The herbicide was applied alone or with adjuvants included in the spray solution. A backpack sprayer equipped with four 8002 flat fan spray nozzles operated at 30 psi covering a swath of 7 feet was used for the applications. The application volume was 20 gallons per acre of spray solution. The coverage was typical of a commercial application. The applications were made at approximately 11:00 AM on a hot dry July day. The temperature was 98 F. and relative humidity was only 12%. At one hour after the herbicide application a simulated hard rainstorm on 2 mm of water was applied to half of each plot using a high volume sprayer discharging approximately 60 gallons per minute at 30 psi. with the spray directed towards the weeds. The rainfall delivery to the weeds was typical of a tropical shower or a desert thunderstorm. Herbicide performance was evaluated visually by a skilled experimenter 15 days after treatment.

| Herbicide (Rate) | Tank Mix Adjuvant | Simulated Rain | % Broadleaf Control (*Portulaca oleracea*) | % Grass Control (*Eichinochloa crus-galli*) |
|---|---|---|---|---|
| Glyphos® 0.5 qt/acre | None | No | 47.5 | 47.5 |
| Glyphos® 0.5 qt/acre | None | Yes | 27.5 | 20.0 |
| Glyphos® 0.5 qt/acre | SILICONE SURFACTANT A | No | 60.0 | 57.5 |

| Herbicide (Rate) | Tank Mix Adjuvant | Simulated Rain | % Broadleaf Control (*Portulaca oleracea*) | % Grass Control (*Eichinochloa crus-galli*) |
|---|---|---|---|---|
| Glyphos ® 0.5 qt/acre | SILICONE SURFACTANT A | Yes | 30.0 | 30.0 |
| Glyphos ® 0.5 qt/acre | SILICONE SURFACTANT B | No | 75.0 | 75.0 |
| Glyphos ® 0.5 gt/acre | SILICONE SURFACTANT B | Yes | 62.5 | 30.0 |

All adjuvant rates were 0.1% v/v of the spray solution.

SILICONE SURFACTANTS A and B were both effective in enhancing the control of both the broadleaf weed, Common Purslane, and barnyard grass by glyphosate under these very low humidity environmental conditions. Also both adjuvants improved the rainfastness of the glyphosate. These results clearly show that the non-spreading siloxanes, as defined in this patent, can enhance glyphosate performance on grasses and broadleaves under very low humidity conditions without the need of a humectant. Prior art (e.g., Monsanto Patent WO 89/12394) teaches that super spreading trisiloxanes require the addition of a humectant to be efficacious under low relative humidity.

The above description of the invention is intending to be illustrative and not limiting. Various changes or modification in the embodiments described may occur to those skilled in the art. These changes can be made without departing from the scope or spirit of the invention.

What is claimed is:

1. A herbicidal composition which comprises a herbicide, which is effective against herbaceous plants, optionally one or more cosurfactants and one or more silicone surfactants of the formula $$R_3Si-O-[RR'SiO-]_n-O-SiR_3$$

wherein
n is 1 to 3,
R is an alkyl radical with 1 to 6 carbon atoms,
R' is a radical of the structure $$-(CH_2)_m-O-(C_2H_4O)_y(C_2H_3R"O)_z-Z,$$

wherein
m is 2 to 6,
R" is independently methyl, ethyl or phenyl,
Z is hydrogen, an alkyl radical with 1 to 4 carbon atoms, or an acyl radical with 2 to 6 carbon atoms,
y is 6 to 30,
z is 1 to 10,
with the proviso that the ratio of y to z is 1 or greater, and that the total number of alkylene oxide groups n*(y+z) in the siloxane polymer (I) is at least 12 whereby said silicone surfactant in a 0.10% aqueous solution exhibits a surface tension of less than about 30 mN/m and a spreading area on a polypropylene surface of about 10% or less compared to that of a superspreading siloxane sufactant of the formula $$Me_3SiO[MeR^1SiO]_1-OSiMe_3$$

where $R^1$ is $-(CH_2)_3-O-(CH_2CH_2-O)_8-Me$.

2. The herbicidal compositions of claim 1, wherein
n is 1,
R and R" are methyl,
m is 3,
y is 8 to 30,
z is 2 to 10 and
Z is hydrogen, methyl or acetyl, and the ratio of y to z is 2 to 10.

3. The herbicidal compositions of claim 2, wherein the ratio of y to z is 2 to 6.

4. The herbicidal compositions of claim 1, wherein n is 2, R and R" is methyl, m is 3, y is 5 to 20, z is 1 to 6 and Z is hydrogen, methyl or acetyl and the ratio of y to z is 2 to 10.

5. The herbecidal compositions of claim 4, wherein the ratio of y to z is 2 to 6.

6. The herbicidal compositions of claim 1, wherein the herbicide is the herbicide is N-(phosphonomethyl)glycine or a salt thereof.

7. The herbicidal compositions of claim 1, wherein said composition comprises 1 to 50% by weight of one or several non-spreading silicone surfactants.

8. The herbicidal compositions of claim 1, wherein said composition comprises 10 to 70% by weight of one or several non-spreading silicone surfactants and 30 to 90% by weight of one or more organic cosurfactants.

9. The herbicidal compositions of claim 8, wherein said organic cosurfactants are selected from the group of ethoxylated alkyl amines, ethoxylated alkyl quaternary amines and propoxylated quaternary ammonium surfactants, ethoxylated alkyl aryl alcohols and their derivatives, linear and branched alcohol ethoxylates.

10. A method for increasing the rainfastness on herbaceous plants of a herbicidal composition comprising a herbicide, which is effective against herbaceous plants, without increasing its spreading properties which comprises adding to said herbicidal composition an effective amount of one or more silicone surfactants of the formula $$R_3Si-O-[RR'SiO-]_n-O-SiR_3$$

wherein
n is 1 to 3,
R is an alkyl radical with 1 to 6 carbon atoms,
R' is a radical of the structure $$-(CH_2)_m-O-(C_2H_4O)_y(C_2H_3R"O)_z-Z,$$

wherein
m is 2 to 6,
R" is independently methyl, ethyl or phenyl,
Z is hydrogen, an alkyl radical with 1 to 4 carbon atoms, or an acyl radical with 2 to 6 carbon atoms,
y is 6 to 30,
z is 1 to 10,
with the proviso that the ratio of y to z is 1 or greater, and that the total number of alkylene oxide groups n*(y+z) in the siloxane polymer (I) is at least 12 whereby said silicone surfactant in a 0.10% aqueous solution exhibits a surface tension of less than about 30 mN/rn and a spreading area on a polypropylene surface of about 10% or less compared to that of a superspreading siloxane surfactant of the formula

where $R^1$ is —$(CH_2)_3$—O—$(CH_2CH_2$—O$)_8$—Me.

11. The method of claim 10, wherein n is 1, R and R" are methyl, m is 3, y is 13 to 30, z is 1 or 2 and Z is hydrogen, methyl or acetyl.

12. The method of claim 10, wherein n is 2, R and R" is methyl, m is 3, y is 6 to 20, z is 1 or 2 and Z is hydrogen, methyl or acetyl.

13. The method of claim 12, wherein the ratio of y to z is 2 to 6.

14. The method of claim 10, wherein n is 1 R and R" is methyl, m is 3, y is 8 to 30, z is 2 to 10 and Z is hydrogen, methyl or acetyl, and the ratio of y t z is 2 to 10.

15. The method of claim 10, wherein n is 2, R and R" is methyl, m is 3, y is 5 to 20, z is 1 to 6 and Z is hydrogen, methyl or acetyl, and the ratio of y to z is 2 to 10.

16. The method of claim 15, wherein the ratio of y to is 2 to 6.

17. The method of claim 10, wherein the herbicide is N-(phosphonomethyl)glycine or a salt thereof.

18. A method for reducing the run-off on herbaceous plants of a herbicidal composition comprising a herbicide, which is effective against herbaceous plants, without increasing its spreading properties, which comprises adding to said herbicidal composition an effective amount of one or more silicone surfactants of the $R_3Si$—O—[RR'Si—O—]$_n$—O—$SiR_3$ wherein n is 1 to 3, R is an alkyl radical with 1 to 6 carbon atoms, R' is a radical of the structure

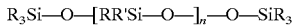

wherein m is 2 to 6,

R" is independently methyl, ethyl or phenyl,

Z is hydrogen, an alkyl radical with 1 to 4 carbon atoms, or an acyl radical with 2 to 6 carbon atoms, Y is 6 to 30, z is 1 to 10, with the proviso that the ratio of y to z is 1 or greater, and that the total number of alkylene oxide groups n*(y+z) in the siloxane polymer (I) is at least 12 whereby said silicone surfactant in a 0.10% aqueous solution exhibits a surface tension of less than about 30 mN/m and a spreading area on a polypropylene surface of a out 10% or less compared to that of a superspreading siloxane surfactant of the formula

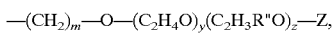

where $R^1$ is —$(CH_2)_3$—O—$(CH_2CH_2$—O$)_8$—Me.

19. The method of claim 18, wherein n is 2, R and R" is methyl, m is 3, y is 13 to 30, z is 1 or 2 and Z is hydrogen, methyl or acetyl.

20. The method of claim 18, wherein n is 2, R and R" is methyl, m is 3, y is 6 to 20, z is 1 or 2 and Z is hydrogen, methyl or acetyl.

21. The method of claim 18, wherein n is 1, R and R" is methyl, m is 3, y is 8 to 30, z is 2 to 10 and Z is hydrogen, methyl or acetyl, and the ratio of y to z is 2 to 10.

22. The method of claim 21, wherein the ratio of y to z is 2 to 6.

23. The method of claim 18, wherein n is 2, R and R" is methyl, m is 3, y is 5 to 20, z is 1 to 6 and Z is hydrogen, methyl or acetyl, and the ratio of y to z is 2 to 10.

24. The method of claim 23, wherein the ratio of y to z is 2 to 6.

25. The method of claim 18, wherein the herbicide is N-(phosphonomethyl)glycine or a salt thereof.

26. A method for improving the efficacy on herbaceous plants of a herbicidal compositions comprising a herbicide, which is effective against herbaceous plants, under conditions of low humidity without the need for humectants and without increasing its spreading properties, which comprises adding to said herbicidal composition an effective amount of one or more silicone surfactants of the formula

wherein n is 1 to 3,

R is an alkyl radical with 1 to 6 carbon atoms,

R' is a radical of the structure

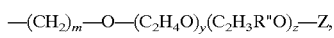

wherein m is 2 to 6,

R" is independently methyl, ethyl or phenyl,

Z is hydrogen, an alkyl radical with 1 to 4 carbon atoms, or an acyl radical with 2 to 6 carbon atoms, y is 6 to 30, z is 1 to 10, with the proviso that the ratio of y to z is 1 or greater, and that the total number of alkylene oxide groups n*(y+z) in the siloxane polymer (I) is at least 12 whereby said silicone surfactant in a 0.10% aqueous solution exhibits a surface tension of less than about 30 mN/m and a spreading area on a polypropylene surface of about 10% or less compared to that of a superspreading siloxane surfactant of the formula

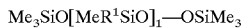

where $R^1$ is —$(CH_2)_3$—O—$(CH_2CH_2$—O$)_8$—Me.

27. The method of claim 26, wherein n is 1, R and R" is methyl, m is 3, y is 13 to 30, z is 1 or 2 and Z is hydrogen, methyl or acetyl.

28. The method of claim 26, wherein n is 2, R and R" is methyl, m is 3, y is 6 to 20, z is 1 or 2 and Z is hydrogen, methyl or acetyl.

29. The method of claim 26, wherein n is 1, R and R" is methyl, m is 3, y is 8 to 30, z is 2 to 10 and Z is hydrogen, methyl or acetyl, and the ratio of y to z is 2 to 10.

30. The method of claim 29, wherein the ratio of y to z is 2 to 6.

31. The method of claim 26, wherein n is 2, R and R" is methyl, m is 3, y is 5 to 20, z is 1 to 6 and Z is hydrogen, methyl or acetyl, and the ratio of y to z is 2 to 10.

32. The method of claim 31, wherein the ratio of y to z is 2 to 6.

33. The method of claim 26, wherein the herbicide is N-(phosphonomethyl)glycine or a salt thereof.

34. A method for improving the efficacy of a herbicidal compositions comprising a herbicide, which is effective against herbaceous plants and one or more cosurfactants selected from the group consisting of ethoxylated alkyl amines, ethoxylated alkyl quaternary amines and propoxylated quaternary ammonium surfactants, ethoxylated alkyl aryl alcohols and their derivatives, linear and branched alcohol ethoxylates on herbaceous plants, which comprises adding to said agrochemical composition an effective amount of one or more silicone surfactants of the formula $$R_3Si-O-[RR'SiO-]_n-O-SiR_3,$$

wherein
n is 1 to 3,
R is an alkyl radical with 1 to 6 carbon atoms,
R' is a radical of the structure $$-(CH_2)_m-O-(C_2H_4O)_y(C_2H_3R''O)_z-Z,$$

wherein
m is 2 to 6,
R" is independently methyl, ethyl or phenyl,
Z is hydrogen, an alkyl radical with 1 to 4 carbon atoms, or an acyl radical with 2 to 6 carbon atoms,
y is 6 to 30,
z is 1 to 10,
with the proviso that the ratio of y to z is 1 or greater, and that the total number of alkylene oxide groups n*(y+z) in the siloxane polymer (I) is at least 12 whereby said silicone sufactant in a 0.10% aqueous solution exhibits a surface tension of less than about 30 mN/m and a spreading area on a polypropylene surface of a out 10% or less compared to that of a superspreading siloxane surfactant of the formula $$Me_3SiO[MeR^1SiO]_1-OSiMe_3$$

where $R^1$ is $-(CH_2)_3-O-(CH_2CH_2-O)_8-Me$.

35. The method of claim 34, wherein n is 1, R and R" is methyl, m is 3, y is 13 to 30, z is 1 or 2 and Z is hydrogen, methyl or acetyl.

36. The method of claim 34, wherein n is 2, R and R" is methyl, m is 3, y is 6 to 20, z is 1 or 2 and Z is hydrogen, methyl or acetyl.

37. The method of claim 34, wherein n is 1, R and R" is methyl, m is 3, y is 8 to 30, z is 2 to 10 and Z is hydrogen, methyl or acetyl, and the ratio of y to z is 2 to 10.

38. The method of claim 37, wherein the ratio of y to z is 2 to 6.

39. The method of claim 34, wherein n is 2, R and R" is methyl, m is 3, y is 5 to 20, z is 1 to 6 and Z is hydrogen, methyl or acetyl, and the ratio of y to z is 2 to 10.

40. The method of claim 39, wherein the ratio of y to z is 2 to 6.

41. The method of claim 34, wherein the herbicide is N-(phosphonomethyl)glycine or a salt thereof.

* * * * *